| United States Patent [19] | [11] | 4,049,450 |
|---|---|---|
| Greenwald | [45] | Sept. 20, 1977 |

[54] 4-HYDROXYPYRAZOLE DEVELOPING AGENTS

[75] Inventor: Richard B. Greenwald, Lexington, Mass.

[73] Assignee: Polaroid Corporation, Cambridge, Mass.

[21] Appl. No.: 671,741

[22] Filed: Mar. 30, 1976

[51] Int. Cl.$^2$ .......................... G03C 5/54; G03C 5/38; G03C 5/30; G03C 1/48

[52] U.S. Cl. .................................. 96/29 R; 96/29 D; 96/61 M; 96/66 HD; 96/76 R; 96/77; 96/95

[58] Field of Search ................. 96/66 HD, 95, 76 R, 96/61 M, 29 R, 29 D, 77

[56] References Cited

U.S. PATENT DOCUMENTS 2,751,300   6/1956   James et al. ..................... 96/66 HD
2,983,606   5/1961   Rogers ............................. 96/66 HD

OTHER PUBLICATIONS

Pyrazoles, Pyrazolines . . . Rings, John Wiley & Sons, NY. 1967, pp. 126–128.
Nye & Tang, "Synthesis of Pyrazol-4-ols," Canadian J. of Chem. 48, 3563 1970.
Freeman et al., "The Nitrosation . . . Derivatives," J. Org. Chem. 34, 187.

Primary Examiner—David Klein
Assistant Examiner—Richard L. Schilling
Attorney, Agent, or Firm—Sybil A. Campbell

[57] ABSTRACT

Certain 4-hydroxypyrazoles are employed as silver halide developing agents which find particular utility in diffusion transfer photographic processes.

23 Claims, No Drawings

4-HYDROXYPYRAZOLE DEVELOPING AGENTS

BACKGROUND OF THE INVENTION

1. Field of the Invention

This invention relates to photography, and more particularly, it relates to compositions and processes useful in the development of photosensitive silver halide emulsions.

2. Description of the Prior Art

In recent years, there has been a growing interest in heterocyclic developing agents, i.e., developers containing a heterocyclic ring as part of their structure. Some of these developing agents have the conventional hydroxyl or amino developing groups substituted on adjacent carbon atoms of a heterocyclic ring to provide structures similar to those of the developing agents in the aliphatic and aromatic series. Still other heterocylic developing agents have one of the functional developing groups included as part of the heterocyclic ring. Illustrative developing agents of the latter type include 1-phenyl-3-pyrazolidone and its 4,4-dialkyl derivatives which form the subject matter of U.S. Pat. No. 2,289,367 and 2,772,282, respectively, and 1-phenyl-4-amino-5-pyrazolones which form the subject matter of U.S. Pat. No. 2,895,825.

The present invention is concerned with the use of certain 4-hydroxy pyrazoles as silver halide developing agents.

SUMMARY OF THE INVENTION

It is therefore the primary object of the present invention to provide a new class of photographic silver halide developing agents which are particularly useful in diffusion transfer processes.

It is another object of this present invention to provide photographic processes, products and compositions employing said silver halide developing agents.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

Detailed Description of the Invention

Specifically, the photographic developing agents of the present invention may be represented by the following formula:

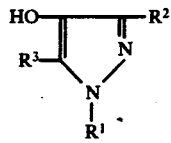

wherein $R^1$ is selected from hydrogen and hydroxy and $R^2$ and $R^3$ each is selected from phenyl, 2-thienyl and alkyl. Preferably, the alkyl group is lower alkyl having 1 to 4 carbon atoms, such as, methyl, ethyl, propyl, isopropyl, n-butyl and t-butyl. The phenyl, 2-thienyl and alkyl groups in turn may be substituted, for example, with solubilizing groups, such as, hydroxy, carboxy, amino and alkyl ethers.

Specific examples of compounds useful in the present invention are as follows:

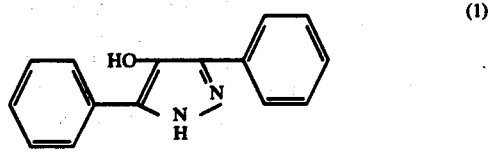

(1)

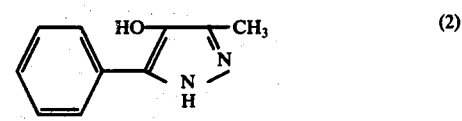

(2)

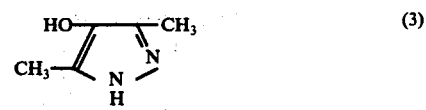

(3)

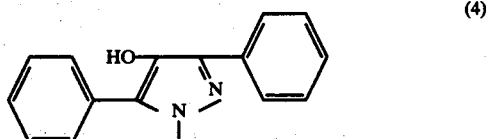

(4)

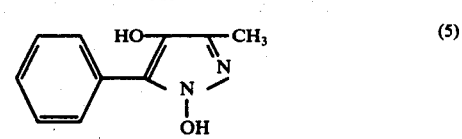

(5)

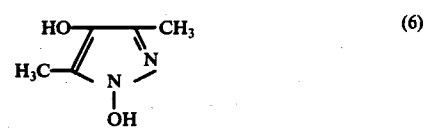

(6)

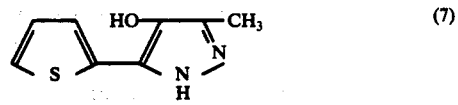

(7)

Alkyl-and/or aryl-substituted 4-hydroxypyrazoles and 1,4-dihydroxypyrazoles are known. For example, the compounds of formulas (1) to (6) above and their preparation have been described in the literature as follows:

| Compound | Reference |
| --- | --- |
| (1) | Can. J. Chem. 48, 3563 |
| (2) | Ber. 35, 3318 |
| (3) | Ber. 35, 3307 |
| (4) | J. Org. Chem. 34, 187 |
| (5) | J. Org. Chem. 34, 187 |
| (6) | J. Org. Chem. 34, 187 |

The thienyl-substituted pyrazoles may be prepared according to known procedures. For example, the compound of formula (7) was prepared as follows:

a. Ethyl-2-thiophenecarboxylate (25g., 0.16M) and potassium t-butoxide (18g., 0.16M) in 250 mls. dry toluene was stirred together for 15 minutes, then cooled in an ice bath. Acetone (9.28g., 0.16M) was added dropwise with stirring and cooling over about ½ hour. After addition was complete, the reaction mixture was stirred for 3 hours in the ice bath and allowed to stand at room temperature overnight. After cooling in an ice bath, 250 mls. of water was added with stirring. The aqueous layer was separated and the organic layer was extracted with water (3 × 50 mls.). The combined aqueous extracts were washed with ethyl ether (3 × 100 mls.) then treated with 10.4 mls. of acetic acid and finally extracted with ethyl ether (4 × 75 mls.). The combined ether extracts were dried over magnesium sulfate. The ether was stripped in vacuo to give about 12g. of crude material which was fractionated under reduced pressure. The fraction boiling at about 135° – 140° C./4mm. was collected yielding 10g. of 2,4-dioxo-4-(2-thienyl)butane.

b. The product of step (a) (4.6g. 27.3 mM.) in 45 mls. of ethyl ether was treated with freshly distilled sulfuryl chloride (3.7 g., 27.3mM.) in the cold. The solution was allowed to warm to room temperature and then heated to reflux for 2 hours. The ethereal solution was transferred to a separatory funnel, washed with water (4 × 25 mls.) and then dried over magnesium sulfate. The ether was stripped in vacuo to give 5.3g. of semisolid which was fractionated (148° – 50° C./4 mm.) to yield 4.8g. of 2,4-dioxo-3-chloro-4-(2-thienyl)butane.

c. The product of step (b) (4.8g., 23.8 mM.) was added to a hot solution of potassium acetate (4.7g., 47.6 mM.) in 20 mls. of acetic acid. The solution was heated in an oil bath at 130° C. for 3 hours, cooled and filtered. The acetic acid was stirred in vacuo and the residue treated with ethyl ether and water. The ether layer was washed with water, 10% potassium bicarbonate, water and dried over sodium sulfate. The ether was stripped in vacuo to yield 2.5g. of 2,4-dioxo-3-acetoxy-4-(2-thienyl)butane.

d. The product of step (c) (25g., 11mM.) in 25 mls. of ethanol was treated with $N_2H_4.H_2O$ (1.1g., 22.2mM.) and heated on a steam bath for 30 minutes. The ethanol was stripped in vacuo to yield 2.8g. of brown semi-solids which was treated with chloroform on a steam bath. The mixture was cooled and filtered to give 1.3g. of beige crystalline material which was recrystallized from water/ethanol (80:20) to yield 800 mgs. of the title compound.

It will be appreciated that other compounds within the scope of the present invention may be prepared according to the foregoing procedures.

As indicated above, the 4-hydroxypyrazoles comprising the developing agents of the present invention while useful in conventional or "tray" development find particularly utility in diffusion transfer processes for forming images in silver or in color. Such processes are now well known in the art; see for example, U.S. Pat. Nos. 2,543,181; 2,647,056; 2,983,606; 3,719,489; etc. in processes of this type, an exposed silver halide emulsion is treated with a processing composition whereby the exposed silver halide emulsion is developed and an imagewise distribution of diffusible image-forming components is formed in the unexposed and undeveloped portions of the silver halide emulsion. This distribution of image-forming components is transferred by imbibition to an image-receiving stratum in superposed relationship with the silver halide emulsion to provide the desired transfer image.

In silver diffusion transfer processes, processing of the exposed silver halide emulsion is effected in the presence of a silver halide solvent, such as sodium thiosulfate or uracil, which forms a diffusible complex with the undeveloped silver halide. The soluble silver complex thus formed diffuses to the superposed image-receiving layer where the transferred silver ions are deposited as metallic silver to provide the silver transfer image.

In preparing silver prints in this manner, the image-receiving layer preferably includes certain materials, the presence of which, during the transfer process has a desirable effect on the amount and character of silver precipitated on the image-receiving element. Materials of this type are specifically described in U.S. Pat. Nos. 2,690,237 and 2,698,245, both issued in the name of Edwin H. Land on Dec. 28, 1954 and U.S. Pat. No. 3,671,241 of Edwin H. Land issued on June 20, 1972.

The photosensitive element may be any of those conventionally used in silver diffusion transfer processes and generally comprises a silver halide emulsion carried on a base, e.g., glass, paper or plastic film. The silver halide may be a silver chloride, iodide, bromide, iodobromide, chlorobromide, etc. The binder for the halide, though usually gelatin, may be a suitable polymer such as polyvinyl alcohol, polyvinyl pyrrolidone and their copolymers.

Separating the photosensitive element from the image-receiving layer may be controlled so that the layer of processing composition is removed from the image-receiving layer or the layer of processing composition is caused to remain in contact with the image-receiving layer, e.g., to provide it with a protective coating. Techniques which enable such results to be accomplished as desired are described in U.S. Pat. No. 2,647,054 issued to Edwin H. Land on July 28, 1953. In general, the processing reagents are selected so that traces remaining after the solidified processing layer has been separated from the silver image or which remain in said layer adhered as a protective coating on the silver image are colorless or pale, so as not to appreciably affect the appearance of the image and to have little or no tendency to adversely react with the silver image.

The developing agents of the present invention also may be employed in diffusion transfer processes adapted to provide positive silver transfer images which may be viewed as positive transparencies without being separated from the developed negative silver image including such processes adapted for use in forming additive color projection positive images. Diffusion transfer processes of this type are described in U.S. Pat. Nos. 3,536,488 of Edwin H. Land and 3,615,428 of Lucretia J. Weed and in U.S. application Ser. No. 383,196 of Edwin H. Land filed July 27, 1973 now U.S. Pat. No. 3,894,871.

The subject developing agents also may be employed in diffusion transfer processes where the final image is in dye, and as appropriate for the particular color process, the developing agent may be used as the principal developer, for example, in the processes of aforementioned U.S. Pat. No. 3,719,489 or as an auxiliary developer, for example, in the processes of aforementioned U.S. Pat. No. 2,983,606. In these diffusion transfer processes, a photosensitive component comprising at least one photosensitive silver halide emulsion having a dye image-providing compound associated therewith in the same or in an adjacent layer is exposed to form a developable image then developed with a processing composition to form an imagewise distribution of a soluble and diffusible image-providing material which is transferred, at least in part, by diffusion, to a superposed image-receiving component comprising at least a dyeable stratum. These processes relay for color image formation upon a differential in mobility or solubility of dye image-providing material obtained as a function of development so as to provide an imagewise distribution of such material which is more diffusible and which, therefore, may be selectively transferred to the superposed dyeable stratum. The differential in mobility or solubility may be obtained, for example, by a chemical action such as a redox reaction, a silver ion-assisted cleavage reaction or a coupling reaction.

The dye image-providing materials which may be employed in such processes generally may be characterized as either (1) initially soluble or diffusible in the processing composition but which are selectively rendered non-diffusible in an imagewise pattern as a function of development; or (2) initially insoluble or non-diffusible in the processing composition but which are selectively rendered diffusible in an imagewise pattern as a function of development. These materials may be complete dyes or dye intermediate, e.g., color couplers.

Examples of initially soluble or diffusible materials and their use in color diffusion transfer processes are disclosed, for example, in U.S. Pat. Nos. 3,087,817; 2,661,293; 2,693,244; 2,698,798; 2,802,735; and 2,983,606. Examples of initially non-diffusible materials and their use in color transfer systems are disclosed in U.S. Pat. Nos. 3,443,939; 3,443,940; 3,227,550; 3,227,551; 3,227,552; 3,227,554; 3,243,294; 3,445,228; 3,719,488 and 3,719,489.

In any of these systems, multicolor images may be obtained by employing a photosensitive element containing at least two selectively sensitized silver halide layers each having associated therewith a dye image-providing material exhibiting the desired spectral absorption characteristics. The most commonly employed elements of this type are the so-called tripack structures employing a blue-, a green- and a red-sensitive silver halide layer having associated therewith, respectively, a yellow, a magenta and a cyan image-providing material.

The photosensitive and image-receiving elements may be separate components which are brought together during processing and thereafter retained together as the final print or separated following image formation; or they may together comprise a unitary structure, e.g., an integral negative-positive film structure wherein the negative and positive, i.e., the photosensitive element and image-receiving element are laminated and/or otherwise physically retained together at least prior to image formation. Integral negative-positive film structures adapted for forming color transfer images viewable without separation, i.e. wherein the image-receiving component containing the dye transfer image need not be separated from the photosensitive component for viewing purposes are described and claimed in U.S. Pat. Nos. 3,415,644; 3,415,645; 3,415,646; 3,573,043 and 3,573,044 in the name of Edwin H. Land and in U.S. Pat. Nos. 3,594,164 and 3,594,165 in the name of Howard G. Rogers.

In conventional development and in diffusion transfer photographic processes, the subject compounds may be used as the sole silver halide developing agent, or they may be employed in combination with another silver halide developing agent as an auxiliary developer or as the main component of the developing combination. Examples of developing agents that may be used in combination with the subject compounds include hydroquinone and substituted hydroquinones, such as, tertiary butyl hydroquinone, 2,5-dimethyl hydroquinone, methoxyhydroquinone, ethoxyhydroquinone, chlorohydroquinone; pyrogallol and catechols, such as, catechol, 4-phenyl catechol and tertiary butyl catechol; aminophenols, such as, 2,4,6-triaminophenol, 2,4-diaminophenol dihydrochloride and 4,6-diamino-orthocresol; 1,4-diaminobenzenes, such as, p-phenylenediamine, 1,2,4-triaminobenzene and 4-amino-2-methyl-N,N-diethylaniline; ascorbic acid and its derivatives, such as, ascorbic acid, isoascorbic acid and 5,6-isopropylidine ascorbic acid; and hydroxylamines, such as N,N-di-(2-ethoxyethyl) hydroxylamine and N,N-di(2-methoxyethoxyethyl) hydroxylamine.

When the compounds of the present invention are used in diffusion transfer processes, the processing composition if it is to be applied to the emulsion by being spread thereon in a thin layer usually includes a film-forming thickening agent. The processing composition may comprise, for example, one or more developing agents of the present invention and optionally, one or more conventional developing agents such as those enumerated above, an alkali such as sodium hydroxide or potassium hydroxide and a viscosity-increasing agent such as a high molecular weight polymer, e.g., sodium carboxymethyl cellulose, hydroxyethyl cellulose, or carboxymethyl hydroxyethyl cellulose. As noted above, in the production of silver transfer image, a silver halide solvent is employed which may be included in the processing composition, or if desired, a silver halide solvent precursor such as those disclosed in U.S. Pat. No. 3,698,898 of J. Michael Grasshoff and Lloyd D. Taylor may be disposed in a layer of the film unit. In addition to the above ingredients, the processing composition may be further modified by the inclusion of restrainers, preservatives and other components commonly employed in developer compositions. All these materials are preferably in aqueous solution.

Rather than being dissolved in the aqueous alkaline processing composition prior to application thereof to an exposed silver halide emulsion, the developing agents of the present invention may be disposed prior to exposure in the photosensitive element, e.g., by placing them in, on or behind a silver halide emulsion layer. In this instance, the processing composition containing the developing agent is formed by application to the photosensitive element of an aqueous alkaline solution capable of solubilizing the developing agent. In diffusion transfer processes, the subject developing agents usually are contained in the processing composition. Whether the developing agent is initially disposed in the processing composition or in the photosensitive element, upon application of the processing composition, the developing agent is provided for processing the photoexposed silver halide material.

To illustrate the utility of the above-defined compounds as photographic developing agents, a photosensitive silver iodobromide emulsion on a support was exposed to a step wedge and processed by spreading a layer of processing composition approximately 1.2 mils. thick between the exposed emulsion and a superposed image-receiving element comprising a layer of regenerated cellulose containing collodial palladium sulfide carried on a transparent support. The processing composition was prepared by adding a developing agent of the present invention in a concentration of 5% by weight to the following formulation:

| | |
|---|---|
| Water | 814.0 g. |
| Potassium hydroxide (Aqueous 50% w/w solution) | 348.0 g. |
| Hydroxyethyl cellulose | 35.0 g. |
| Zinc acetate | 15.0 g. |

-continued

| Triethanolamine | 5.6 g. |
| Uracil | 50.0 g. |

After an imbibition period of approximately one minute, the developed silver halide emulsion was separated from the image-receiving element, and the maximum and minimum transmission densities were measured for the positive image.

The compounds added to the base formulation as developing agents, and the density measurements for the positive image obtained with each of the compounds are set forth in Table I:

TABLE I

| Compound | Density | |
| (Formula No.) | Maximum | Minimum |
| --- | --- | --- |
| (2) | 0.83 | 0.01 |
| (3) | 0.56 | 0.17 |
| (4) | 0.73 | 0.03 |
| (5) | 0.93 | 0.01 |

The foregoing procedure was repeated using the same photosensitive and image-receiving elements and a processing composition that was the same except that sodium hydroxide (348.0 g.-aqueous 50% w/w solution) was substituted for potassium hydroxide and sodium thiosulfate (50.0 g.) was substituted for uracil. Developing agents of the present invention were added to the processing composition in a concentration of 5% by weight. The photosensitive element was exposed and processed in the same manner described above and after an imbibition period of about one minute, the photosensitive and image-receiving elements were separated and the maximum and minimum transfer densities were measured for the positive image.

The compounds added to the latter processing composition as developing agents and the transmission density measurements for the positive image obtained with each of the compounds are set forth in Table II.

TABLE II

| Compound | Density | |
| (Formula No.) | Maximum | Minimum |
| --- | --- | --- |
| (2) | 0.40 | 0.01 |
| (7) | 0.40 | 0.01 |

It will be apparent that the relative proportions of the subject developing agents and of the other ingredients of the processing compositions may be varied to suit the requirements of a given photographic system. Also, it is within the scope of this invention to modify the formulations set forth above by the substitution of alkalies, antifoggants and so forth than those specifically mentioned. Where desirable, it is also contemplated to include in the processing compositions, other components as commonly used in the photographic art.

As mentioned above, rather than being dissolved in the aqueous alkaline processing composition prior to application thereof to an exposed silver halide emulsion, it is also contemplated that the developing agents of the present invention may be disposed prior to exposure in a layer or layers of the photographic film unit, e.g., by placing them in or behind a silver halide emulsion layer in the photosensitive element. In this instance, the processing composition containing the developing agents is formed by application to the photosensitive element of an aqueous alkaline solution capable of solubilizing the developing agent.

Since certain changes may be made in the above compositions and processes without departing from the scope of the invention herein involved, it is intended that all matter contained in the above description should be interpreted as illustrative and not in a limiting sense.

What is claimed is:

1. A method of developing a silver halide emulsion which comprises treating an exposed silver halide emulsion layer carried on a support with an aqueous alkaline processing composition of a silver halide developing agent of the formula wherein $R^1$ is selected from hydrogen and hydroxy and $R^2$ and $R^3$ each is selected from phenyl, 2-thienyl and alkyl.

2. A method as defined in claim 1 wherein said silver halide developing agent is in a layer of a photosensitive element including said silver halide emulsion, and said solution of said developing agent is formed by applying to said photosensitive element a solution of aqueous alkali in which said developing agent is soluble.

3. A method as defined in claim 1 wherein said $R^1$ is hydrogen.

4. A method as defined in claim 1 wherein said $R^1$ is hydroxy.

5. A method as defined in claim 1 wherein said developing agent is

6. A method as defined in claim 1 wherein said developing agent is

7. A method as defined in claim 1 wherein said developing agent is

8. A method as defined in claim 1 wherein said developing agent is

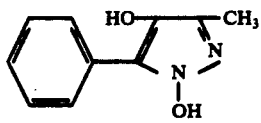

9. A method as defined in claim 1 wherein said developing agent is

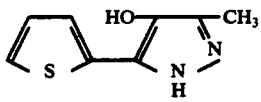

10. A method as defined in claim 1 wherein said developing agent is

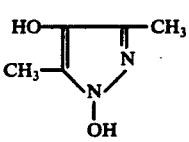

11. A method as defined in claim 1 wherein a dye image-providing material is associated with said silver halide emulsion and which includes the additional step of transferring an imagewise distribution of dye image-providing material to a superposed dyeable stratum to form a dye transfer image.

12. A method as defined in claim 1 wherein said processing composition includes a silver halide solvent and said silver halide emulsion is developed in the presence of an image-receiving material superposed on said emulsion to form a silver transfer image on said image-receiving material.

13. A method as defined in claim 12 wherein said processing composition additionally includes a viscosity-increasing agent.

14. A photographic product comprising a support, a silver halide emulsion carried on said support and a developing agent in a layer on the same side of said support as said silver halide emulsion, said developing agent having the formula

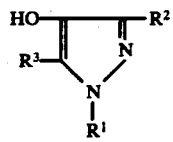

wherein $R^1$ is selected from hydrogen and hydroxy and $R^2$ and $R^3$ each is selected from phenyl, 2-thienyl and alkyl.

15. A product as defined in claim 14 wherein said $R^1$ is hydrogen.

16. A product as defined in claim 14 wherein said $R^1$ is hydroxy.

17. A product as defined in claim 14 wherein said developing agent is

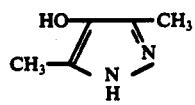

18. A product as defined in claim 14 wherein said developing agent is

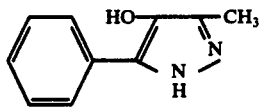

19. A product as defined in claim 14 wherein said developing agent is

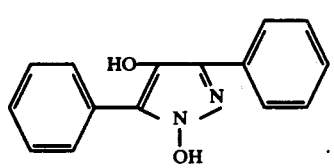

20. A product as defined in claim 14 wherein said developing agent is

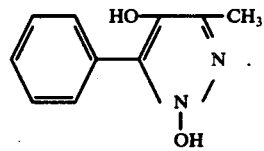

21. A product as defined in claim 14 wherein said developing agent is

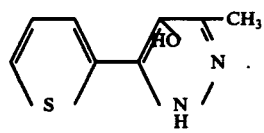

22. A product as defined in claim 14 wherein said developing agent is

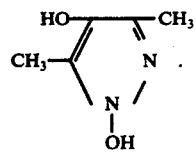

23. A product as defined in claim 17 which additionally includes a dye image-providing material associated with said silver halide emulsion and a dyeable stratum in superposed relationship with said silver halide emulsion.

* * * * *